(12) United States Patent
Xie

(10) Patent No.: US 12,743,197 B2
(45) Date of Patent: Sep. 22, 2026

(54) METHODS, MEDIUMS, AND SYSTEMS FOR PROCESSING CUSTOM FIELD FORMULAS

(71) Applicant: Waters Technologies Ireland Limited, Dublin (IE)

(72) Inventor: Rong Xie, Hudson, MA (US)

(73) Assignee: Waters Technologies Ireland Limited, Dublin (IE)

( * ) Notice: Subject to any disclaimer, the term of this patent is extended or adjusted under 35 U.S.C. 154(b) by 0 days.

(21) Appl. No.: 18/156,053

(22) Filed: Jan. 18, 2023

(65) Prior Publication Data

US 2023/0229299 A1 Jul. 20, 2023

Related U.S. Application Data

(60) Provisional application No. 63/300,397, filed on Jan. 18, 2022.

(51) Int. Cl.
*G06F 3/048* (2013.01)
*G06F 3/0482* (2013.01)
*G06F 3/04847* (2022.01)
*G06F 16/22* (2019.01)
*G16C 20/90* (2019.01)

(52) U.S. Cl.
CPC ........ *G06F 3/04847* (2013.01); *G06F 3/0482* (2013.01); *G06F 16/2291* (2019.01); *G16C 20/90* (2019.02)

(58) Field of Classification Search
CPC ............... G06F 3/04847; G06F 3/0482; G06F 16/2291; G16C 20/90; G16H 40/63; G16H 10/40
See application file for complete search history.

(56) References Cited

U.S. PATENT DOCUMENTS

2007/0033519 A1* 2/2007 Zdenek .................. G06F 40/18 715/234
2013/0080373 A1* 3/2013 Yeck ..................... G16B 50/30 706/50
2022/0019323 A1* 1/2022 Nhan ................. G06F 3/04847

OTHER PUBLICATIONS

Sonny (https://answers.microsoft.com/en-us/msoffice/forum/all/how-do-i-prevent-excel-from-automatically-locking/8a35ad6c-150c-430d-b3a4-13e50b081044), Mar. 4, 2020 (Year: 2020).*
International Search Report and Written Opinion for International Patent Application No. PCT/IB2023/050433, mailed Apr. 21, 2023.
(Continued)

*Primary Examiner* — Aleksey Olshannikov
(74) *Attorney, Agent, or Firm* — Goodwin Procter LLP

(57) ABSTRACT

Exemplary embodiments provide computer-implemented methods, mediums, and apparatuses configured to import, create, and edit formulas for custom fields in an analytical chemistry system. The custom fields may be represented as a tree structure with nodes representing operators. When the custom field is defined, it may be incorporated into a workflow for the analytical chemistry system. Dependencies within the custom field may be identified and the custom field may be incorporated into the workflow at an appropriate workflow stage. The custom field may be scoped to define which elements of a data acquisition the custom field operates over. Various visualization options are described to allow the custom field to be displayed and/or edited in different ways.

20 Claims, 11 Drawing Sheets

(56) References Cited

OTHER PUBLICATIONS

Agg Software: "Process data from the lab equipment", Dec. 9, 2021, pp. 1-10, Retrieved from the Internet: URL:https://web.archive.org/web/2021120907 3527/https://www.aggsoft.com/asd1-exce1-real-time-charting.htm [retrieved on Apr. 8, 2023].

Agg Software: "Export data and update charts in Excel in real-time", Dec. 9, 2021, pp. 1-6, Retrieved from the Internet: URL:https://web.archive.org/web/2021120910 0012/https://www.aggsoft.com/asd1-exce1-real-time-charting- export.htm [retrieved on Apr. 8, 2023].

International Preliminary Report on Patentability for International Patent Application No. PCT/IB2023/050433, mailed Aug. 2, 2024.

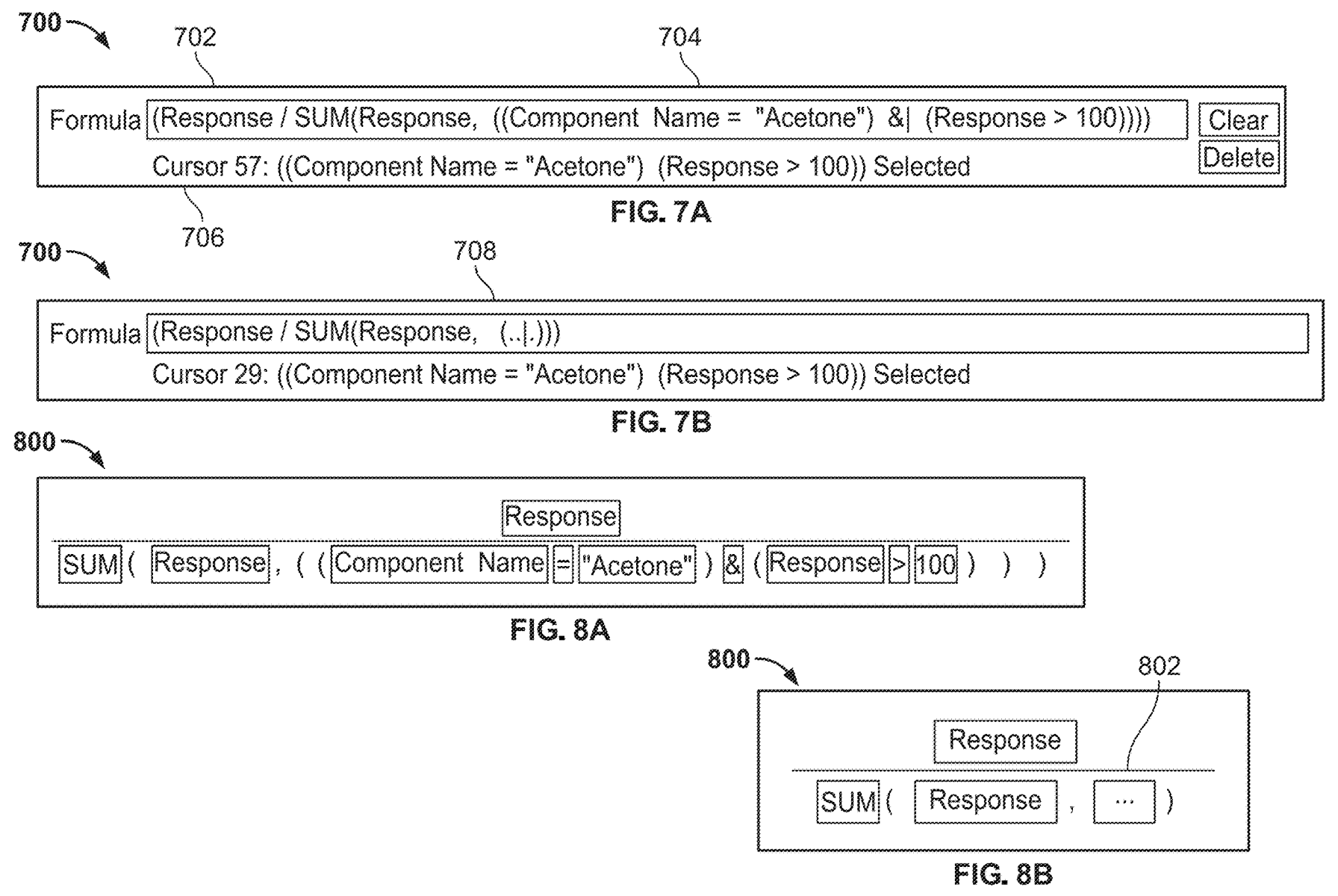

* cited by examiner 700
702
704
Formula (Response / SUM(Response, ((Component Name = "Acetone") &| (Response > 100))))
Clear
Delete
Cursor 57: ((Component Name = "Acetone") (Response > 100)) Selected
706

FIG. 7A 700
708
Formula (Response / SUM(Response, (..|.)))
Cursor 29: ((Component Name = "Acetone") (Response > 100)) Selected

FIG. 7B

800
Response
SUM ( Response , ( ( Component Name = "Acetone" ) & ( Response > 100 ) ) )

FIG. 8A 800
802
Response
SUM ( Response , ··· )

FIG. 8B

METHODS, MEDIUMS, AND SYSTEMS FOR PROCESSING CUSTOM FIELD FORMULAS

CROSS-REFERENCE TO RELATED APPLICATIONS

This application claims the benefit of and priority to U.S. Provisional Patent Application No. 63/300,397, filed Jan. 18, 2022. The entire disclosure of which is hereby incorporated by reference.

BACKGROUND

Laboratory analytical instruments are devices for qualitatively and/or quantitatively analyzing samples. They are often used in a laboratory setting as part of an analytical chemistry system for scientific research or testing. Such devices may measure the chemical makeup of a sample, determine the quantity of components in a sample, and perform similar analyses. Examples of laboratory analytical instruments include mass spectrometers, chromatographs, titrators, spectrometers, elemental analyzers, particle size analyzers, rheometers, thermal analyzers, etc.

As a laboratory analytical instrument generates data, it may store the data in a data structure such as a table. The data structure may include fields storing values for variables. For instance, a field might be a column in a table representing values for a particular measurement across multiple different samples or experiments.

BRIEF SUMMARY

In some cases, a user may wish to define their own custom fields that are based on the fields defined by the laboratory analytical instrument or experiment, or that are based on other custom fields (or a combination of both). By way of example, one of the fields in the data might store the amount of a component detected in a sample. A user might wish to know the average amount of the component detected across a set of samples, and so might define a custom field that performs this calculation.

In practice, defining custom fields often involves performing detailed calculations with complex mathematical formulas. In these circumstances, it can be difficult for a user to visualize what they are doing, and it is relatively easy to make mistakes when defining custom field formulas. Thus, exemplary embodiments relate to improved techniques for defining formulas for custom fields that provide improved visualizations, represent the custom field formulas in more intuitive ways, and allow for more complicated custom fields to be defined with a reduced risk of errors.

Exemplary embodiments may include computer-implemented methods, as well as non-transitory computer-readable mediums storing instructions for performing the methods, apparatuses configured to perform the methods, etc.

In one embodiment, data from a laboratory analytical instrument may be accessed. The data may be organized into one or more fields. The data may represent, for example, information captured by the laboratory analytical instrument in order to analyze a sample (e.g., identifying the components of the sample, the amounts of the components, the purity and/or potency of the sample, etc.). A field may be a grouping of values for a particular variable or variables—for example, a field may be conceptualized as a vector representing a collection of data elements of the same type.

The laboratory analytical instrument may be associated with an analytical method encoded in a workflow. An analytical method may represent a set of steps performed in a specified order to analyze the data. It may involve specifications of algorithms to be performed during the analysis and values used to parameterize the algorithms. A method may be, for example, a sequence of steps used to confirm the identity, quality, purity, and potency of samples being tested. A workflow may capture a particular method in an analytical chemistry system and allow the method to be performed on one or more computers.

A request may be received to define a custom field for use in a stage of the workflow. A custom field may be a field containing values not directly or explicitly measured by the laboratory analytical instrument. Custom fields may be derived from other fields (whether expressly measured by the laboratory analytical instrument or other custom fields) and/or constants, among other possibilities.

In order to define the custom field, an interface may display a formula editor workspace that includes a list of the one or more fields of the data, a list of available operators, and a formula editor. Operators may accept one or more inputs referred to as operands (which may be, for example, arrays of data values such as a vector or matrix), manipulate the input, and generate an output. Operators may be, for instance, vector operators that treat the field as a collection and return a scalar or a subset of the collection. Operators may also or alternatively be vectorized operators that are applied to the elements of the operands and return a vector of the same size as one or both of the operands. Operators may be arithmetic operators or logical operators, among other types.

The formula editor may include one or more interactive placeholders configured to accept an operator or an operand. The placeholders may represent empty nodes into which an operator or operand, respectively, can be placed. A selection of one of the available operators may be received, and the selected operator may be incorporated into the custom field in place of the placeholder. Alternatively or in addition, selection of one of the one or more fields may be received, and the selected field may be incorporated into the custom field in place of the placeholder.

This technique for building a custom field formula differs from conventional techniques, which generally relied on parsing the formula as it was entered. In such conventional techniques, a user would type the formula into an edit box, and the entered text would be parsed simultaneously in order to transform the typed formula into a suitable structure. When a user mistyped part of the formula, the structure would be built incorrectly. Moreover, if the formula were entered with errors (e.g., missing parentheses, accidental deletions, etc.), error validation could be very difficult.

The first embodiment allows the formula to be built as a set of interconnected nodes without parsing the formula during creation. This results in fewer errors and simpler validation. It also allows the formula to be rendered more simply, as described below in connection with the fourth and fifth embodiments. Moreover, because of the way that the custom field is created, the nodes can be stored as a data model or object model. Consequently, the custom field is more readily extensible than with conventional parsing-based techniques.

The thus-created custom field may be associated with the stage of the workflow, where the associating makes the custom field accessible to the workflow. When the workflow is run, it may access the custom field and perform the calculations defined by the custom field's formula.

In a second embodiment, a value for the custom field may be computed during the stage of the workflow with which it is associated. This allows the custom field to be dynamically defined. For example, a custom field may rely on fields calculated at several stages of the workflow. The latest stage of the workflow that generates a field required by the custom field may be selected as the associated stage when the custom field is created, and the custom field may be calculated during this stage. This allows the custom field to rely on data calculated at multiple different workflow stages.

For example, a stage processor may process custom fields when they are created or modified. To process the custom field, the stage processor may: collect all custom field calculations at a processing stage; order the calculations by dependency; parse constants in each formula as scalar; loop the injections or components of the analysis according to the defined scope of each calculation (see the third embodiment below) to retrieve the fields used in the calculation and fill all the nodes that use the same field; calculate result for each node from bottom up; fill the final result for the custom field; and fill any error or warning code for the custom field.

In a third embodiment, the analytical method may perform measurements on one or more injections into the laboratory analytical instrument, each injection including one or more components. An injection may be, for example, an injection of a particular sample into the laboratory analytical instrument for measurement by the laboratory analytical instrument. The sample may be divisible by the laboratory analytical instrument into the components. Components may be, for example, molecules, compounds, elements, etc.

A scope for the custom field may be received, where the scope specifies that the custom field calculation should be applied to all the components in each injection, for each component across all the injections, or for all components across all the injections. By scoping the custom field in this manner, a user can define which elements in the operands will be used to compute the custom field. This provides a greater degree of control over the custom field than was conventionally available.

In a fourth embodiment, a selection of a tree view interface element may be received. In response, the custom field may be displayed as a tree including a set of nodes representing operators and a set of leaf nodes representing operands. This provides an easy-to-read view of the custom formula that allows a user to more effectively visualize and troubleshoot the formula. Because the formula is defined and represented as a set of nodes representing operators, it can be turned into a tree view quickly and efficiently.

In a fifth embodiment, a selection of a formula renderer interface element may be received. In response, the custom field may be displayed in a formula renderer view in a mathematical notation. This provides a more formal view of the custom field. The formula can be rendered efficiently and correctly due to the structure of the custom field (represented as a tree including a set of nodes), especially when the formula includes one or more division operators (particularly in the case of multiple division operators). Portions of the mathematical notation may be collapsible (based on the tree structure of the custom field) to simplify the formula view and allow the user to troubleshoot the custom field.

In a sixth embodiment, a textual representation of the custom field may be displayed in a text box in the interface. The text box may be configured to receive a pasted formula from a clipboard but may also be configured not to allow the formula to be edited within the text box. This enforces the underlying tree structure of the custom field, which provides the advantages noted above. Allowing the user to paste (but not edit) formulas in the edit box provides a degree of backwards compatibility for custom fields generated in parse-based environment. The formula pasted into the text box may be transformed into a tree structure by identifying operators in the formula and recursively defining operands for the operators.

As in the fifth embodiment, the textual representation in the sixth embodiment can be collapsed based on the tree structure to improve readability.

In a seventh embodiment, a cursor may be displayed at a location in the text box corresponding to a current editing action for the custom field. For example, the cursor location may be analyzed after the formula is converted into nodes. Depending on where the cursor is located in the corresponding tree structure of the custom field, the interface may present different options:

- When an empty node is selected, an operator, a field, or a constant can be added/inserted to the empty node. A formula from another custom field can also be inserted into the empty node.
- When the body of a non-empty node is selected, it can be replaced by another (compatible) operator, a field, or a constant. A formula from another custom field can also be inserted into the node. The non-empty node can also be deleted or cleared.
- When the start of a non-empty node is selected, an operator can be inserted to the left of the node, and the original node then becomes the right operand of the newly inserted operator.
- When the end of a non-empty node is selected, and operator can be inserted to the right of the node, and the original node then becomes the left operand of the newly inserted operator.

The seventh embodiment allows a user to interact with the textual representation of the custom field, but also preserves the advantages of representing the custom field as a tree.

Unless otherwise noted, it is contemplated that each embodiment may be used separately to achieve the advantages specifically identified above. It is also contemplated that the embodiments described above (and elsewhere herein) may be used in any combination to achieve further synergistic effects. Other technical features will be readily apparent to one skilled in the art from the following figures, descriptions, and claims.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 7A illustrates an example of a textual representation view in accordance with one embodiment.

FIG. 7B illustrates an example of a textual representation view in accordance with one embodiment.

FIG. 8A illustrates an example of a mathematical notation view in accordance with one embodiment.

FIG. 8B illustrates an example of a mathematical notation view in accordance with one embodiment.

DETAILED DESCRIPTION

Figure 1:
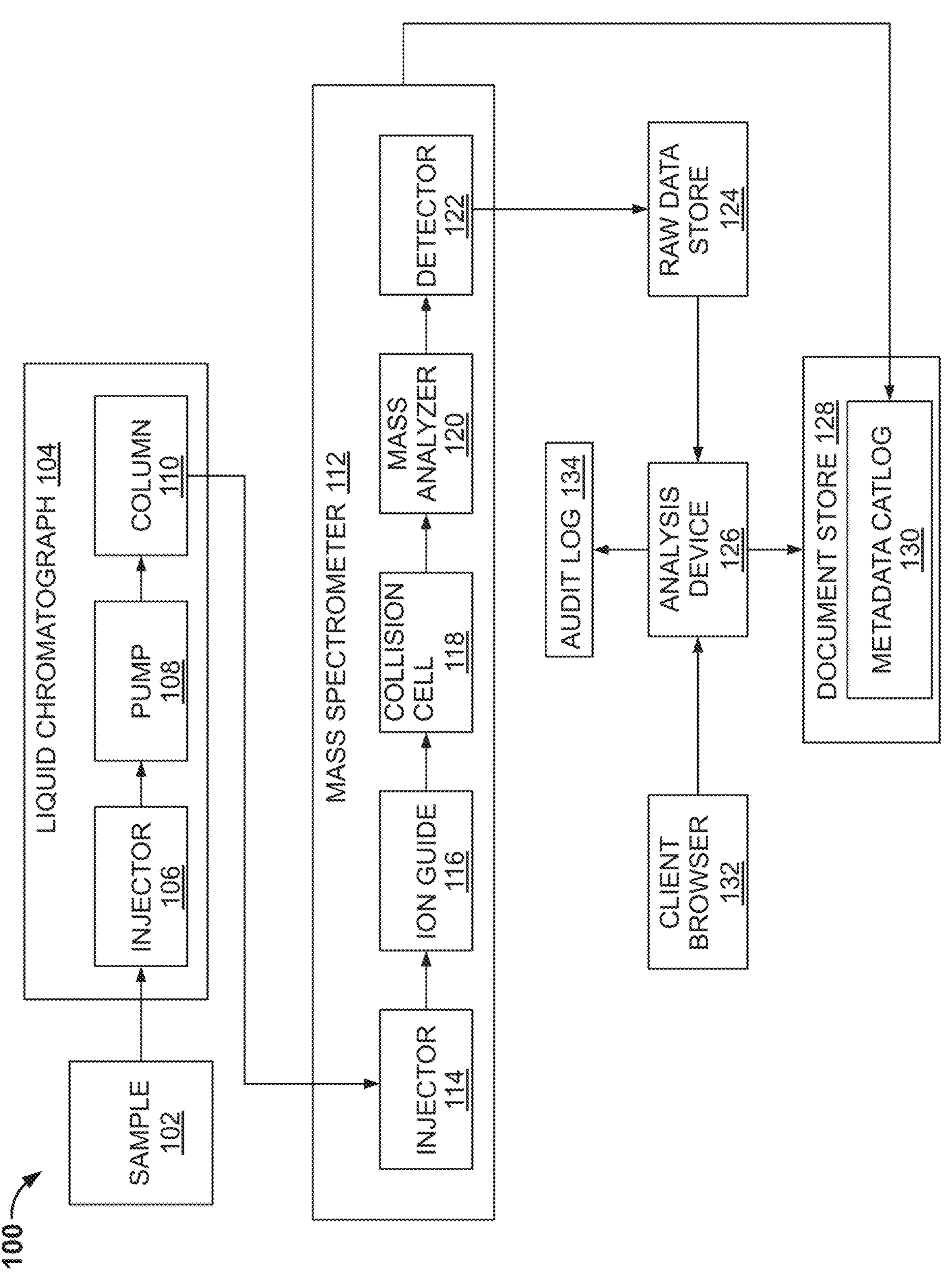
FIG. 1 illustrates an example of a mass spectrometry system according to an exemplary embodiment.

As an aid to understanding, a series of examples will first be presented before detailed descriptions of the underlying implementations are described. It is noted that these examples are intended to be illustrative only and that the present invention is not limited to the embodiments shown.

Reference is now made to the drawings, wherein like reference numerals are used to refer to like elements throughout. In the following description, for purposes of explanation, numerous specific details are set forth in order to provide a thorough understanding thereof. However, the novel embodiments can be practiced without these specific details. In other instances, well known structures and devices are shown in block diagram form in order to facilitate a description thereof. The intention is to cover all modifications, equivalents, and alternatives consistent with the claimed subject matter.

In the Figures and the accompanying description, the designations "a" and "b" and "c" (and similar designators) are intended to be variables representing any positive integer. Thus, for example, if an implementation sets a value for a=5, then a complete set of components 122 illustrated as components 122-1 through **122-*a* may include components 122-1, 122-2, 122-3, 122-4, and 122-5**. The embodiments are not limited in this context.

These and other features will be described in more detail below with reference to the accompanying figures.

For purposes of illustration, FIG. 1 is a schematic diagram of an analytic analytical chemistry system 100 that may be used in connection with techniques herein. Although FIG. 1 depicts particular types of devices in a specific liquid chromatography/mass spectrometry (LCMS) configuration, one of ordinary skill in the art will understand that different types of chromatographic devices (e.g., MS, tandem MS, etc.) may also be used in connection with the present disclosure.

A sample 102 is injected into a liquid chromatograph 104 through an injector 106. A pump 108 pumps the sample through a column 110 to separate the mixture into component parts according to retention time through the column.

The output from the column is input to a mass spectrometer 112 for analysis. Initially, the sample is desolved and ionized by a desolvation/ionization device 114. Desolvation can be any technique for desolvation, including, for example, a heater, a gas, a heater in combination with a gas or other desolvation technique. Ionization can be by any ionization techniques, including for example, electrospray ionization (ESI), atmospheric pressure chemical ionization (APCI), matrix assisted laser desorption (MALDI) or other ionization technique. Ions resulting from the ionization are fed to a collision cell 118 by a voltage gradient being applied to an ion guide 116. Collision cell 118 can be used to pass the ions (low-energy) or to fragment the ions (high-energy).

Different techniques may be used in which an alternating voltage can be applied across the collision cell 118 to cause fragmentation. Spectra are collected for the precursors at low-energy (no collisions) and fragments at high-energy (results of collisions).

The output of collision cell 118 is input to a mass analyzer 120. Mass analyzer 120 can be any mass analyzer, including quadrupole, time-of-flight (TOF), ion trap, magnetic sector mass analyzers as well as combinations thereof. A detector 122 detects ions emanating from mass analyzer 122. Detector 122 can be integral with mass analyzer 120. For example, in the case of a TOF mass analyzer, detector 122 can be a microchannel plate detector that counts intensity of ions, i.e., counts numbers of ions impinging it.

A raw data store 124 may provide permanent storage for storing the ion counts for analysis. For example, raw data store 124 can be an internal or external computer data storage device such as a disk, flash-based storage, and the like. An analysis 126 analyzes the stored data. Data can also be analyzed in real time without requiring storage in a storage medium 124. In real time analysis, detector 122 passes data to be analyzed directly to analysis 126 without first storing it to permanent storage.

Collision cell 118 performs fragmentation of the precursor ions. Fragmentation can be used to determine the primary sequence of a peptide and subsequently lead to the identity of the originating protein. Collision cell 118 includes a gas such as helium, argon, nitrogen, air, or methane. When a charged precursor interacts with gas atoms, the resulting collisions can fragment the precursor by breaking it up into resulting fragment ions. Such fragmentation can be accomplished by switching the voltage in a collision cell between a low voltage state (e.g., low energy, <5 V) and a high voltage state (e.g., high or elevated energy, >15V). High and low voltage may be referred to as high and low energy, since a high or low voltage respectively is used to impart kinetic energy to an ion.

Various protocols can be used to determine when and how to switch the voltage for such an MS/MS acquisition. After data acquisition, the resulting spectra can be extracted from the raw data store 124 and displayed and processed by post-acquisition algorithms in the analysis 126.

Metadata describing various parameters related to data acquisition may be generated alongside the raw data. This information may include a configuration of the liquid chromatograph 104 or mass spectrometer 112 (or other chromatography apparatus that acquires the data), which may define a data type. An identifier (e.g., a key) for a codec that is configured to decode the data may also be stored as part of the metadata and/or with the raw data. The metadata may be stored in a metadata catalog 130 in a document store 128.

The analysis 126 may operate according to a workflow, which describes a scientific method, process, or algorithm used to analyze the data. The workflow may describe how to parameterize hardware, normalize outputs, process data, etc. The analysis 126 may provide visualizations of data to an analyst at each of the workflow steps and allowing the analyst to generate output data by performing processing specific to the workflow step. The workflow may be generated and retrieved via a client browser 132. As the analysis 126 performs the steps of the workflow, it may read raw data from a stream of data located in the raw data store 124. As the analysis 126 performs the steps of the workflow, it may generate processed data that is stored in a metadata catalog 130 in a document store 128; alternatively or in addition, the processed data may be stored in a different location specified by a user of the analysis 126. It may also generate audit records that may be stored in an audit log 134.

Figure 11:
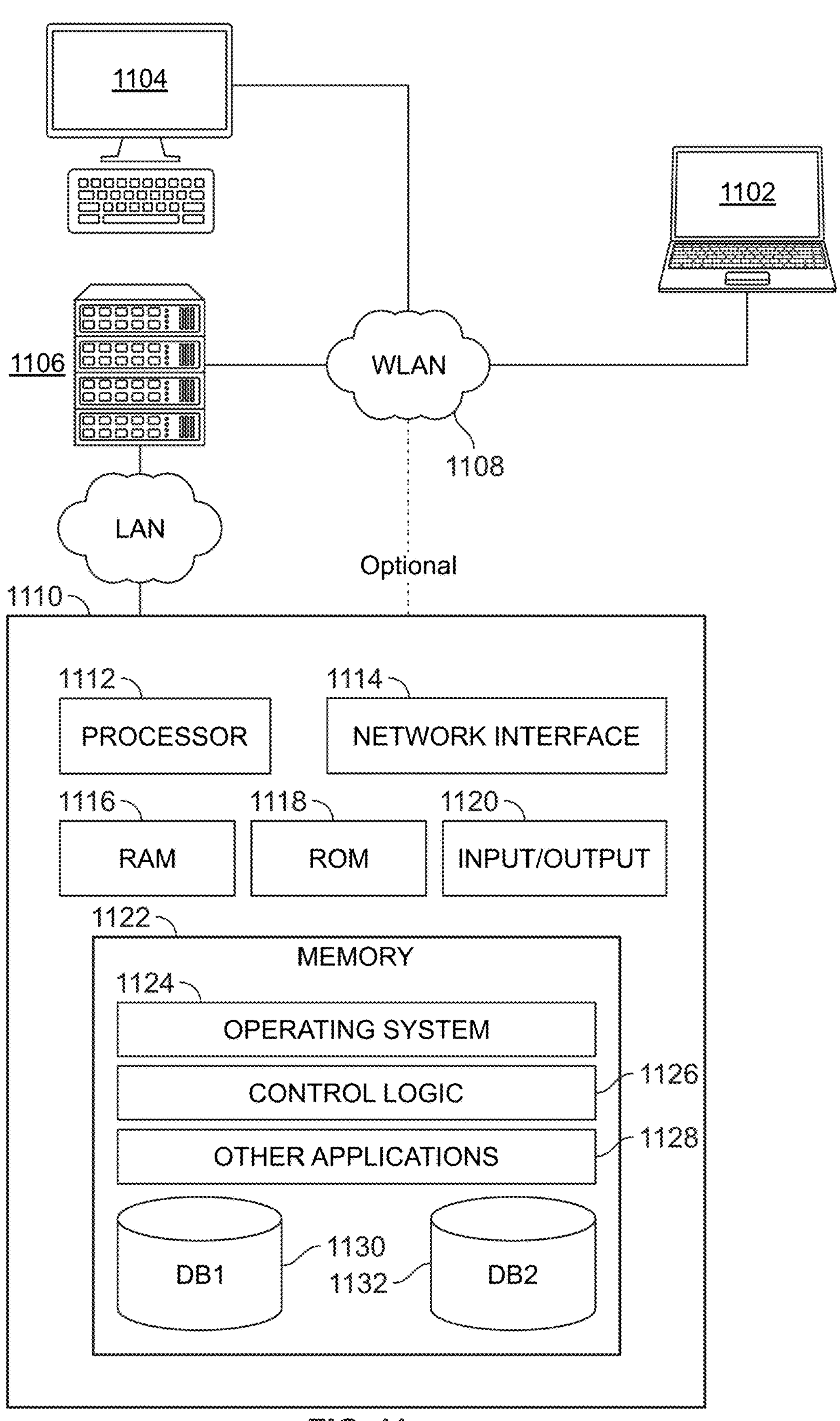
FIG. 11 depicts an illustrative computer system architecture that may be used to practice exemplary embodiments described herein.

The exemplary embodiments described herein may be performed at the client browser 132 and analysis 126, among other locations. An example of a device suitable for use as an analysis 126 and/or client browser 132, as well as various data storage devices, is depicted in FIG. 11.

Figure 2:
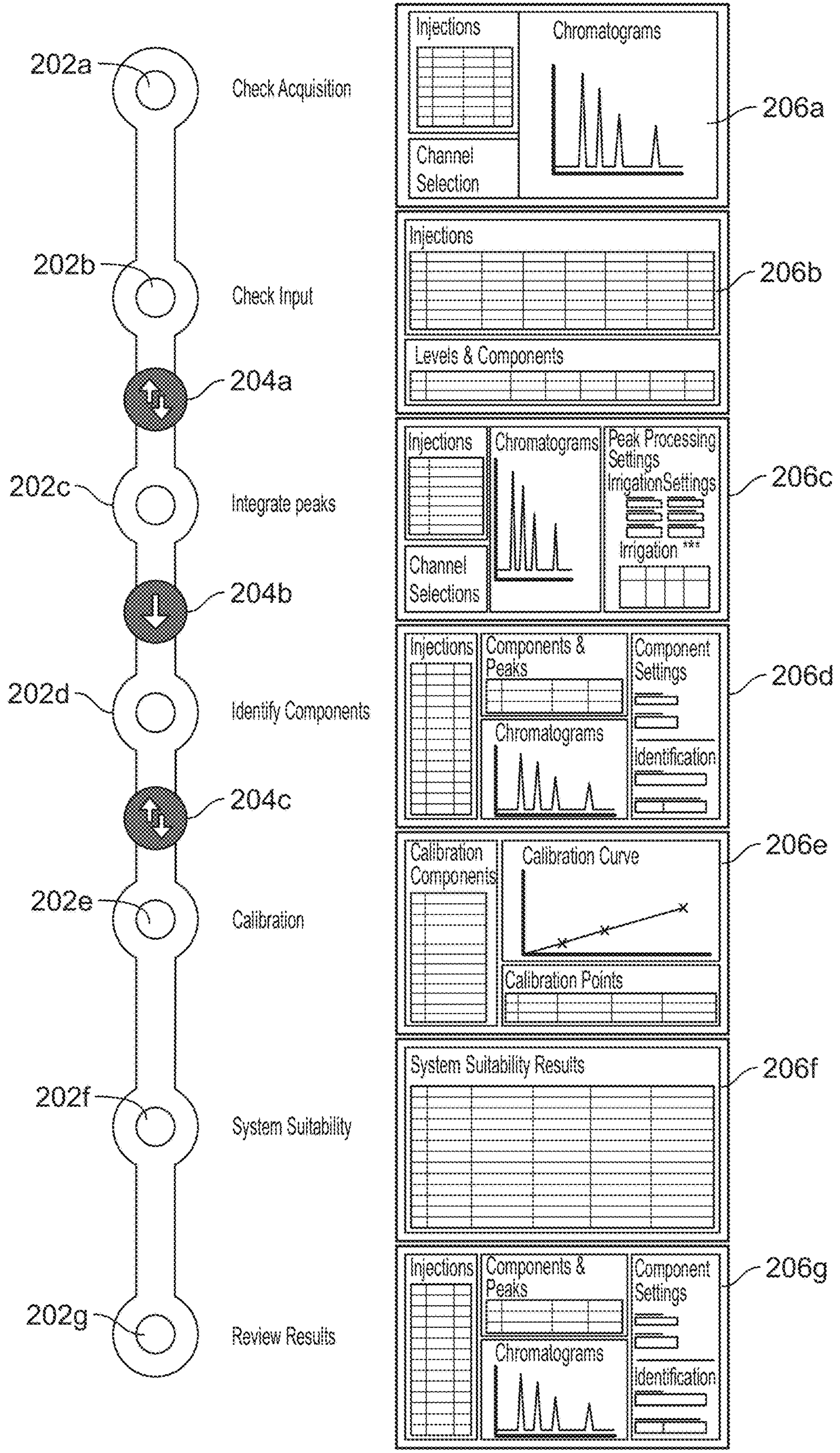
FIG. 2 depicts an exemplary interface for a workflow builder, including workflow steps, transitions, and visualizations associated with each step, according to an exemplary embodiment.

FIG. 2 depicts an example of a way that a workflow may be displayed in a user interface of a workflow builder (e.g., as might be displayed on the client browser 132 previously described).

In the user interface, a set of steps 202*a*-202*g* are arranged in an order. The user may be provided with a set of steps that can be arranged on the interface, or may select from a number of pregenerated templates. The user may be permitted to move the steps in the order, although the workflow builder may enforce a relative ordering of certain steps (e.g., requiring that the integrate peaks step 202*c* be performed before the calibration step 202*e*).

Some or all of the steps may be separated by transitions 204*a*-204*c*. The transitions may be associated with a direction (e.g., allowing movement in the forward direction in the order, a reverse direction, or a forward direction and a reverse direction). The application implementing the workflow may enforce the transitions by only allowing movement in the workflow as indicated by the transitions. At each of the transitions, the application may enforce a change in data stewardship; responsibility for the data may be changed from a group of users associated with the steps before the transition to a group of users associated with the steps after the transition. The application may require that the group of users relinquishing and/or acquiring data access rights provide a signature.

Each of the steps 202*a*-202*g* may be associated with one or more pages defining different configurations for the steps (e.g., configurations and arrangements of visualization elements, settings for the step and/or visualization elements, etc.). The workflow builder may receive, via a user interface, a selection of one of the steps 202*a*-202*g* and, in response, may display images of the pages available for use with the selected step. The images may show different configurations and arrangements of the visualization elements for the step. Upon receiving a selection of an image associated with one of the pages, the system may associate that page with the selected step. The page may define instructions as to how to arrange and configure the visualization elements/step. The application implementing the workflow may retrieve the page definitions and apply them to configure the visualization elements/steps being implemented by the application. FIG. 2 provides examples of pages 206*a*-206*g* that have been selected for, and associated with, each of the steps 202*a*-202*g*.

The data output by the analytical chemistry system 100 may be stored in tables and organized into fields that represent values for a particular measurement across multiple different samples or experiments. More generally, a field may be a collection of data elements of the same type. Custom fields may be used at different stages in the workflow. Custom fields may define user-specified formulas that can be used in the processing performed by the workflow. In some embodiments, users may manually enter custom fields using a keyboard during data acquisition or in a method editor.

In some analytical chemistry systems, fields (including custom fields) may be interpreted as vectors. When the vector contains only one element, the field becomes a scalar. A custom field is defined by a formula that operates on other fields, constants, and operators to generate a user-specified result.

Operators may be divided into two types: vector operators and vectorized operators. Vector operators (or functions) may treat the field over which they operate as a collection and return a scalar or a subset of the collection (for example summary statistical functions). Examples of vector operators include counting the number of valid data points in a field, averaging the data points, computing the standard deviation or variance of the field, determining the maximum or minimum element of a field, returning the element at a given index, etc. Vectorized operators are those in which the operator is applied to the elements of the operands and returns a vector of the same size as at least one of the operands. For example, using the addition operand "+", the formula "a+b" requires that field "a" and "b" are same size vectors, or one of them is a scalar:

(1) a+b={a[i]+b[i]} if a and b are same size vector, (2) a+b={a+b[i]} if a is scalar, (3) a+b={a[i]+b} if b is scalar, or (4) a+b=invalid (null) if both a and b are vectors but size is different.

The operand(s) of an operator may be:

A constant as a scalar

Another field as a vector

Another operator as a nested operation

In a custom field, the elements in the vector may be determined by the scope of the calculation and the object containing the data elements of the field, which the field is associated to.

For example, consider an experiment that involves injecting a compound containing three components (A, B, and C) into an analytical chemistry system and then measuring an amount of each component that was detected. The analytical chemistry system may generate data in a table with a field called "Amount," where "Amount" may be a vector defined by:

Amount={Amount[i]} where i is the component index

The amount of each component may be measured for each experimental run, where another sample of the compound is injected into the analytical chemistry system.

Below is a table showing an example of data collected during three injections of the compound:

| Injection | Component | Amount |
|---|---|---|
| 1 | A | 1 |
| 1 | B | 2 |
| 1 | C | 3 |
| 2 | A | 4 |
| 2 | B | 5 |
| 2 | C | 6 |
| 3 | A | 7 |
| 3 | B | 8 |
| 3 | C | 9 |

We consider a calculation of a custom field called AvgAmount, which calculates the average of its operand (in this case, the Amount field). The scope applied to the calculation may change the results stored in the custom field (and/or the size or other characteristics of the field).

For instance, by default the calculation may be performed for each injection. In this case:

Amount={1, 2, 3} for Injection 1, AVG(Amount)=2

Amount={4, 5, 6} for Injection 2, AVG(Amount)=5

Amount={7, 8, 9} for Injection 3, AVG(Amount)=8

Another possible scope is "each component across samples." With this scope, the calculation is performed for each component across all 3 injections:

Amount={1, 4, 7} for Component A, AVG(Amount)=4

Amount={2, 5, 8} for Component B, AVG(Amount)=5

Amount={3, 6, 9} for Component C, AVG(Amount)=6

Yet another possible scope is "all components across samples," in which case the calculation is performed once for all components across all 3 injections:

Amount={1, 2, 3, 4, 5, 6, 7, 8, 9}, AVG(Amount)=5

The next table depicts another example that shows how the scope of the calculation setting for a peak custom field affects the result. Consider a peak calculation AvgArea=AVG(Area) for the following data:

| Injection | Channel | Area |
|---|---|---|
| 1 | Ch1 | 1 |
| 1 | Ch1 | 2 |
| 1 | Ch2 | 3 |
| 1 | Ch2 | 4 |
| 2 | Ch1 | 5 |
| 2 | Ch1 | 6 |
| 2 | Ch2 | 7 |
| 2 | Ch2 | 8 |
| 3 | Ch1 | 9 |
| 3 | Ch1 | 10 |
| 3 | Ch2 | 11 |
| 3 | Ch2 | 12 |

When the scope is "Default", the calculation is performed for each channel in each injection:

Area={1, 2} for Ch 1 in Injection 1, AVG(Area)=1.5

Area={3, 4} for Ch 2 in Injection 1, AVG(Area)=3.5

Area={5, 6} for Ch 1 in Injection 2, AVG(Area)=5.5

Area={7, 8} for Ch 2 in Injection 2, AVG(Area)=7.5

Area={9, 10} for Ch 1 in Injection 3, AVG(Area)=9.5

Area={11, 12} for Ch 2 in Injection 3, AVG(Area)=11.5

When the scope is set to "each channel across samples", the calculation is performed for each channel across all 3 injections:

Area={1, 2, 5, 6, 9, 10} for Ch 1 in 3 Injections, AVG(Area)=5.5

Area={3, 4, 7, 8, 11, 12} for Ch 2 in 3 Injections, AVG(Area)=7.5

When the scope is set to "all channels across all samples", the calculation is performed for all channels across all 3 injections:

Area={1, 2, 3, 4, 5, 6, 7, 8, 9, 10, 11, 12} for all channels in all 3 Injections, AVG(Area)=6.5

The available scopes may be dependent on the fields used to organize the data.

Figure 3:
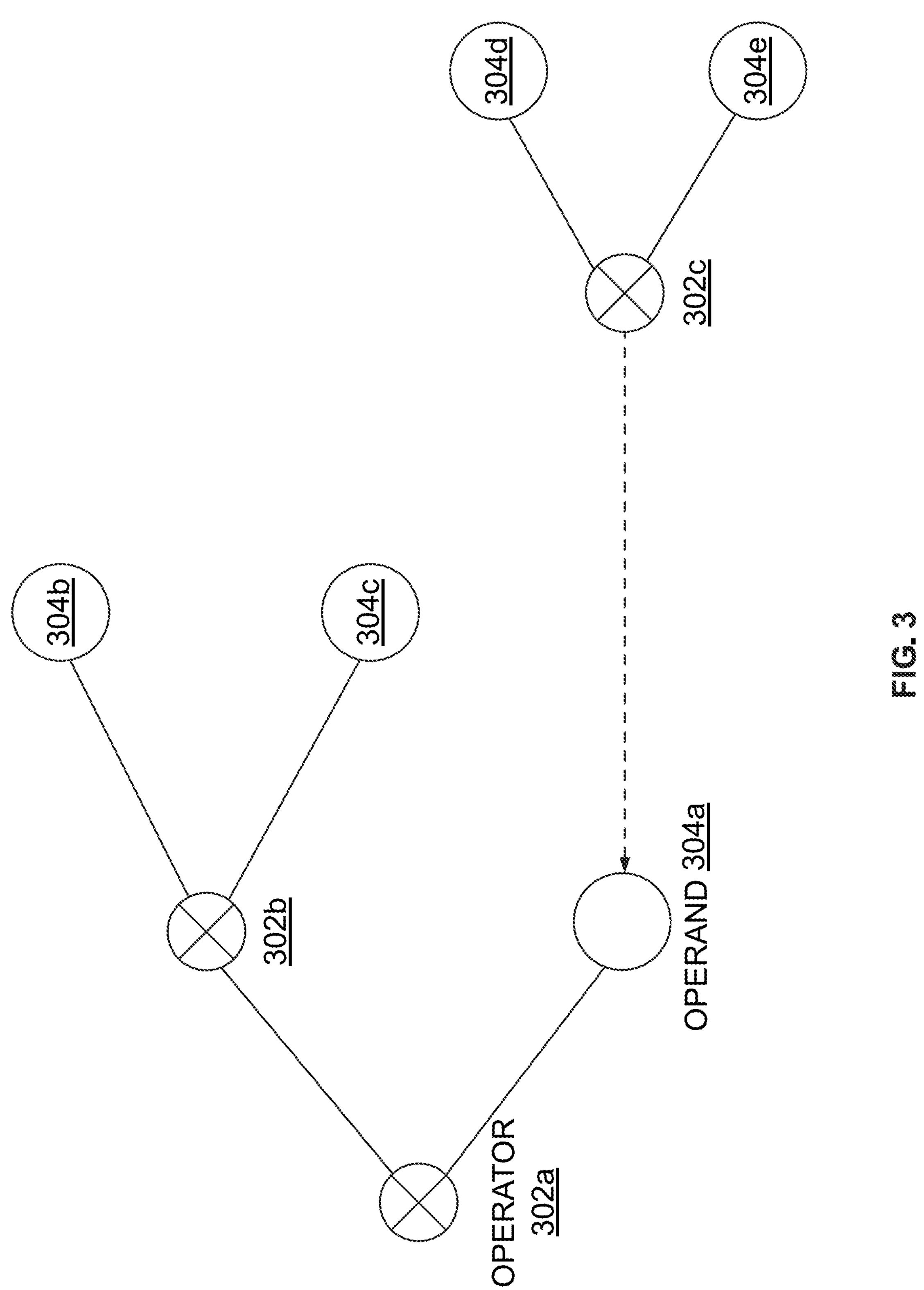
FIG. 3 illustrates an example of a custom field tree structure accordance with one embodiment.

A formula for a custom field may have a recursive tree structure of "nodes". Each "node" may contain an operator and its operands. Each operand may contain a nested node. FIG. 3 depicts an example in which a formula is represented as a tree structure made up of nodes. In this example, any non-leaf node may represent an operator 302*a*, . . . 302*c*. Leaf nodes may represent operands 304*a*, . . . 304*e*. Leaf nodes may themselves represent nested trees (in this case, the operand 304*a* is a nested tree that includes an operator 302*c* that operates on operands 304*d*, 304*e*.

According to exemplary embodiments, a custom field formula may be built using a recursive tree structure as a paradigm. For instance, in FIG. 3 the formula is built in following steps from top down:

Node Operator 1 is added.

Node Operator 2 is attached to the 1st operand of Operator 1.

Operands of Operator 2 are filled with either constant or a field.

Node Operator 3 is attached to the 2nd operand of Operator 2.

Operands of Operator 3 are filled with either constant or a field.

More nodes can be attached to the operands of nested nodes.

In the tree structure, each node may a recursive structure of the following style:

```
class Node {
public string ID;
public string Op;
public List<Node> Operands; }
```

The tree structure may be built graphically in a tree view, using a representation such as the one depicted in FIG. 3. The tree structure may also be built in a formula editor view, in which new nodes are defined to include placeholder operators and operands. A user may select elements from a list of available operators and operands to fill in the placeholders, as in the interface shown in FIG. 4.

The exemplary interface is divided into several different components. A workflow stage viewer 402 shows an overview of the different stages of the workflow used in processing the analytical chemistry data and highlights the currently active stage. The remainder of the interface may differ depending on which workflow stage is currently active—in this example, the "Identify Components" stage is selected, and so options appropriate to this stage are displayed.

For example, the interface includes an injections viewer 404 showing the injections that were run as part of the experiment, and a components viewer 406 showing the components that were identified across the injections. In some embodiments, a user may be able to change the view to display the peaks corresponding to the components or the raw chromatograph data.

Figure 5:
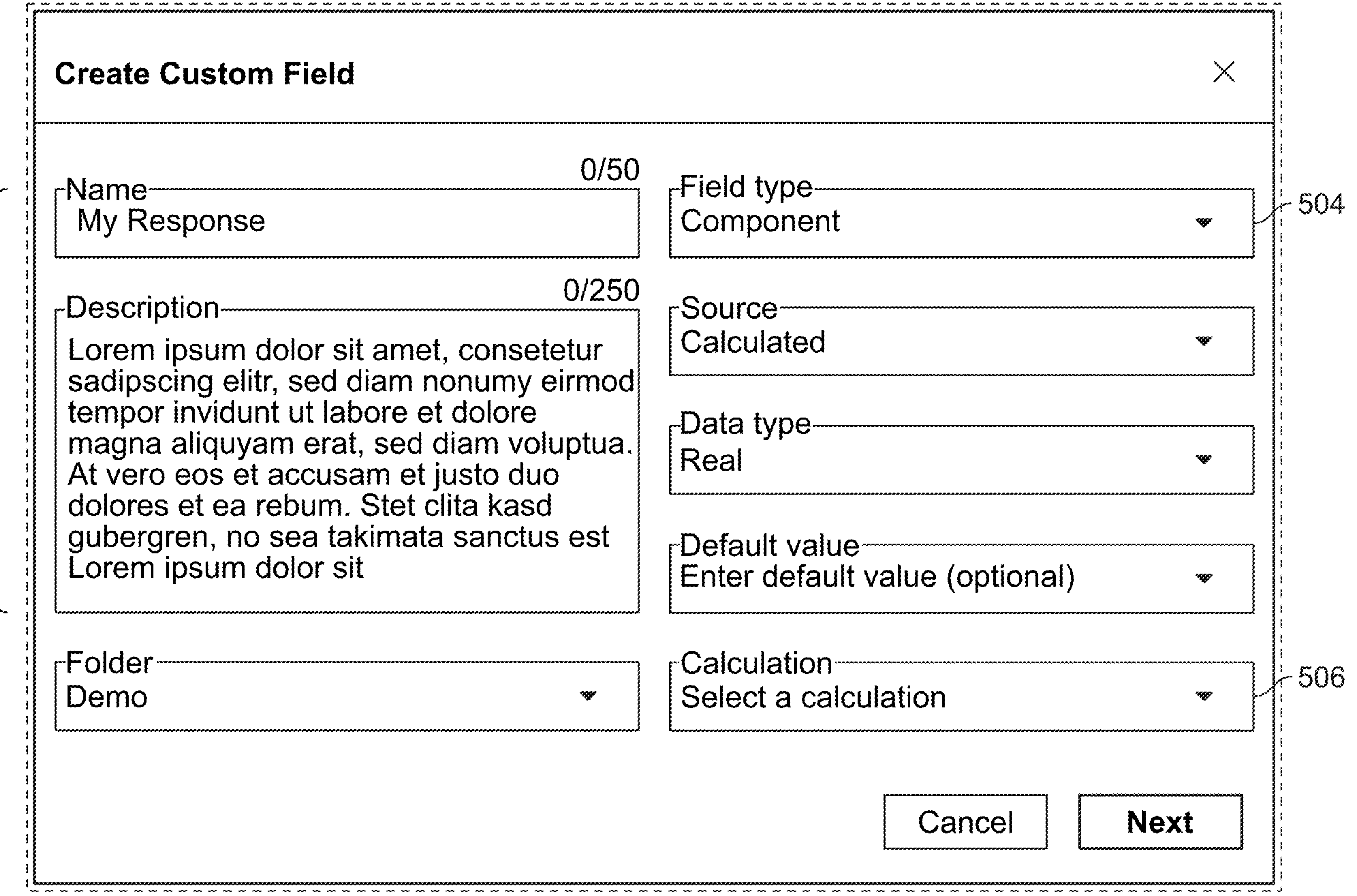
FIG. 5 illustrates an exemplary custom field settings wizard in accordance with one embodiment.

As a user defines custom fields for the data, the custom field may be shown in the interface. The user can select a selected custom field 408 (e.g., from a drop-down menu) for editing in the interface. Upon selection, custom field settings 410 for the custom field may be displayed; some of the options for these settings are shown in FIG. 5.

Figure 4:
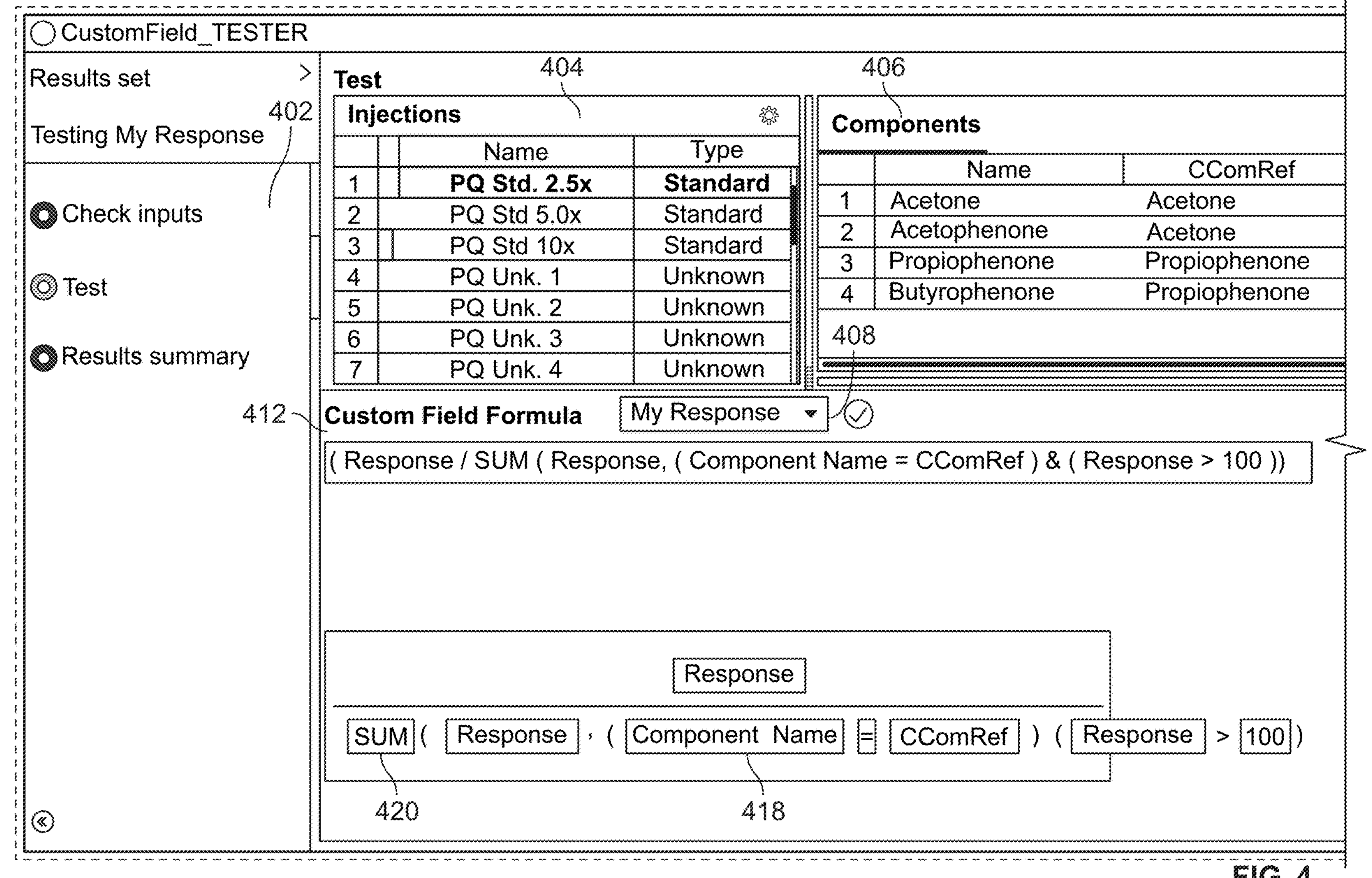
FIG. 4 illustrates an exemplary custom field editor interface in accordance with one embodiment.
Figure 4:
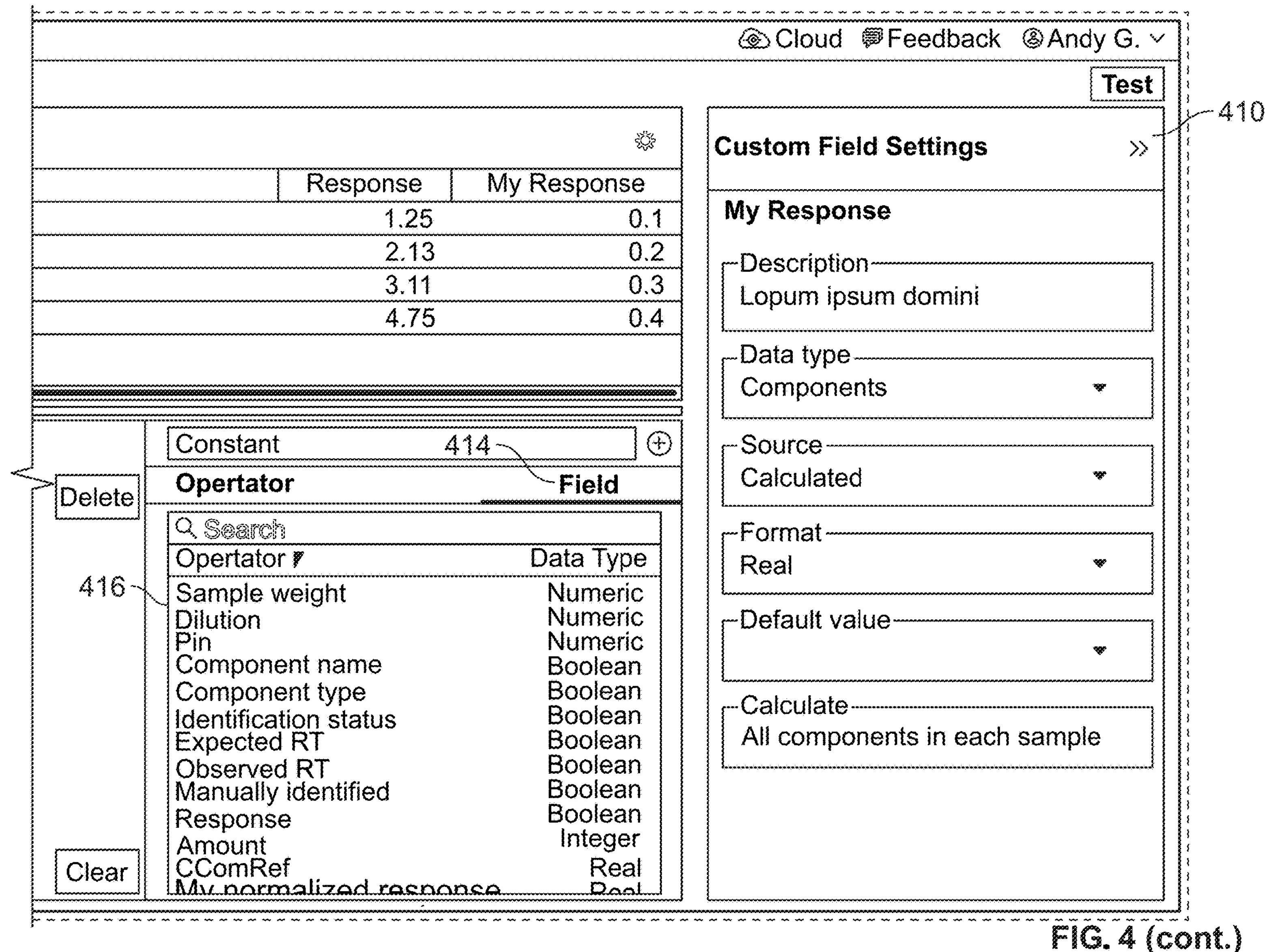

A custom field editor 412 may allow the user to edit the custom field using placeholders. When a new custom field is defined, the custom field may initially be populated by a single interactive placeholder, which is a generic representation that can be replaced by a specific operator and/or operand. As operators are added to replace existing placeholders, new placeholders may be added (depending on how many operands the added operator accepts) so that the custom field formula can grow dynamically. For instance, FIG. 4 shows a placeholder operand 418 and a placeholder operator 420.

A user can interact with a placeholder in a number of ways. For instance:

it can be edited directly for user to type in constant.

it accepts drag-and-drop operators or operands for the user to add or replace the node corresponding to the placeholder. The workspace contains an available operators list 416 and available fields list 414 showing operators and fields, respectively, available for use in

- calculations. A listed operator or field can be dragged and dropped onto the placeholder in the view mentioned above. As soon as an operator or field is dragged and dropped onto an existing placeholder to create a sub node, placeholders are immediately created in the view for the operands of this newly added operator or field.
- the user can mouse over the placeholder, which displays a tooltip. When the placeholder is replaced by a node containing an operator or operands, the node remains interactive (e.g., accepting new values as in the example above) and mousing over the placeholder may display a description of the operator or operands.
- double clicking on the placeholder/node can expand or collapse the node in the formula editor or other related view
- an incomplete node may be highlighted for errors.

As the custom field formula is built in the formula editor, the resulting tree may be validated by applying casting rules. When a first node is added for a custom field, the casting rules may require that the return type from the new node should match or can be casted to the data type of the custom field. When a nested node is added to an operand of parent node, casting rules apply such that a return type from the nested node should match or can be casted to the expected type of the operand.

When an existing node is replaced by a new "identical" node, all the existing operands can be kept without breaking the existing branch. An "identical" node may a node with same number and type of operands. For example, a binary arithmetic operator in a branch can be replaced by another binary arithmetic operator without breaking existing branch.

When an existing node is replaced by a new node with valid return type but the number and type of operands do not match, the existing branch may be broken. When an existing node is replaced by the same operator but different operands (an optional argument, for example), the existing operand(s) of same type may be kept.

When an existing node is deleted, the branch may be broken and the whole formula may become invalid, until the operand it is detached from is filled again with an constant, a field, or a new node.

Additional tabs may allow the user to switch between different views of the formula editor. For example, a tree view tab may allow the formula to be viewed and edited in a tree view (see, e.g., FIG. 3)

FIG. 5 depicts an example of a wizard for custom field settings. The wizard may be displayed in the formula editor interface, or separately as a pop-out window. For instance, the wizard allows various field identifiers 502 to be defined for the field, such as the name of the field, a short name for the field to be displayed in the interface, and/or a brief description of the field.

A field type 504 describes the format for the field (e.g, the type of data structure into which members of the field will be fitted). The field type 504 may thus determine many other settings. Changing the type may cause a backend to refresh to provide different list of fields that are available for the calculation. Some examples of types include a "component" type representing a component of a sample, a "peak" type which is a calculated value, a "sample" type representing a sample in an injection, etc.

Furthermore, the wizard may include scope settings 506, allowing the scope of the field's calculation to be defined as described in detail above.

Figure 6:
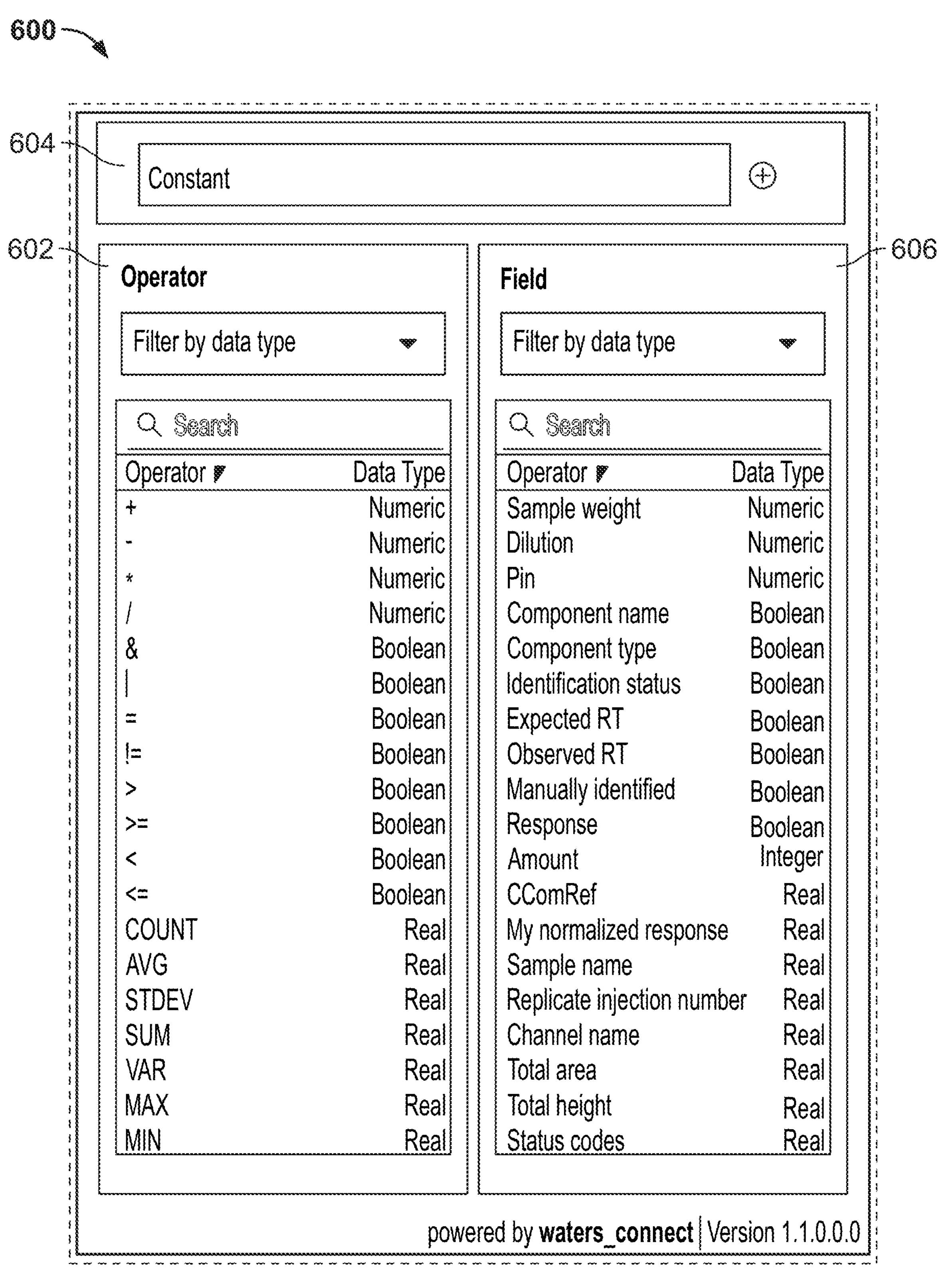
FIG. 6 illustrates an exemplary operator/operand selector in accordance with one embodiment.

FIG. 6 shows an example of an operator and field picker 600, which shows the available operators and fields and may allow a user to select or drag-and-drop items into the formula editor. The operator and field picker 600 may be displayed in the formula editor interface, or separately as a pop-out window.

The operator and field picker 600 may include an available operator list 602, which lists the different operators that may be incorporated into a node. The available operators may depend on which operators are supported by the environment hosting the analytical chemistry system.

A constant entry box 604 may allow a user to enter a value using a keyboard, where the value will be used as a constant in the custom field formula. An available field list 606 displays the different fields that can be used as operands for the custom field.

The formula can optionally be viewed in a text-based mode, as in the textual representation view 700 depicted in FIG. 7A and FIG. 7B. The textual representation view 700 may include a text box 702 that displays a text-based representation of the custom field formula.

The text box 702 may be read-only so that a user cannot edit the formula in the text box 702 (which might destroy the tree structure representing the custom field formula, and which can be an error-prone way to edit custom fields). However, the text box 702 may allow a user to copy-and-paste custom fields. For example, a legacy custom field formula can be copied into the text box 702, which causes the system to parse the custom field formula and convert it into a tree structure representation.

The parser may apply precedence and associativity rules to define a parser grammar for "infix" notation when building the tree structure. One example of such precedence and associativity rules are as follows:

- Parentheses have precedence over all other operators.
- Operator ˆ (exponentiation) has precedence over arithmetic operators /, *, –, and +.
- Binary operators * and / have precedence over – and +.
- Unary operator – has precedence over binary – and +.
- Operator ˆ is right associative while all other operators are left associative.
- Precedence climbing is used.

For example, the first three rules tell us that following formula:

*aˆb*cˆd+eˆf/gˆ(h+i)* is parsed to the following tree:

+(*(ˆ(*a*,*b*),ˆ(*c*,*d*)),/(ˆ(*e*,*f*),ˆ(*g*,+(*h*,*i*))))

while the last rule tells us that a–b–c is parsed to –(–(a, b),c) rather than –(a, –(b,c)), whereas aˆbˆc is parsed to ˆ(a,ˆ(b,c)) rather than ˆ(ˆ(a,b),c), using precedence climbing rule. 1.7.7

The text box 702 may display a cursor location 704 representing a currently selected location within the custom field formula. Although the user may not be able to directly edit the custom field formula at the cursor location 704 in the text box 702, the text box 702 may nonetheless be interactive. For example, a cursor node identifier 706 may display data for the node that exists at the location of the cursor location 704. Optionally, the user may interact with the node using the text box 702 (for example, by double-clicking at the cursor location 704) in order to collapse or expand the node.

For example, FIG. 7B depicts the textual representation view 700 after the user has interacted with the text box 702 at the cursor location 704, causing collapsed text 708 to be displayed in place of the textual representation of the node at the cursor location 704. Double clicking in the collapsed text 708 may cause the text to expand back into the view of FIG. 7A.

While the node is selected in the textual representation view 700, additional options may be presented in the cursor node identifier 706. Although the user might not be able to edit the node in the text box 702, the options in the cursor node identifier 706 might include:

- When an empty node is selected, an operator, a field, or a constant can be added/inserted to the empty node (e.g., using the wizard of FIG. 6). A formula from another custom field can also be inserted into the empty node.
- When the body of a non-empty node is selected, it can be replaced by another (compatible) operator, a field, or a constant. A formula from another custom field can also be inserted into the node. The non-empty node can also be deleted or cleared.
- When the start of a non-empty node is selected, an operator can be inserted to the left of the node, and the original node then becomes the right operand of the newly inserted operator.
- When the end of a non-empty node is selected, and operator can be inserted to the right of the node, and the original node then becomes the left operand of the newly inserted operator.

Another type of view is a mathematical notation view as shown in the formula renderer 800 of FIG. 8A. In this example, the custom field formula is depicted as a mathematical equation using an equation renderer. The user can interact with the formula renderer 800 in a similar manner to the textual representation view 700, such as by collapsing a selected node into a collapsed node 802 as shown in FIG. 8B.

Figure 9:
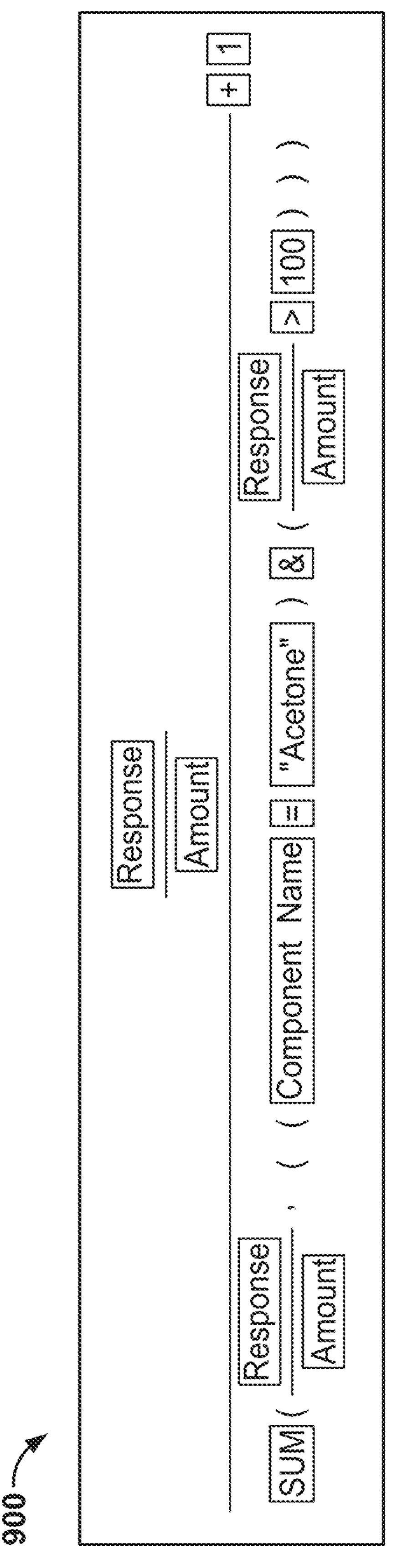
FIG. 9 illustrates an example of a mathematical notation view in accordance with one embodiment.

The formula renderer view is helpful for creating and editing complex formulas, especially those that include multiple division operators. For instance, FIG. 9 depicts a particularly complex formula 900 that includes four division operators. In a different view, such as the textual representation view, the operands of the division operators would be dependent on the numbers and locations of parentheses, which might be complicated and clutter the interface. With the formula renderer view, the operation of nested division operators are much easier to discern.

Figure 10:
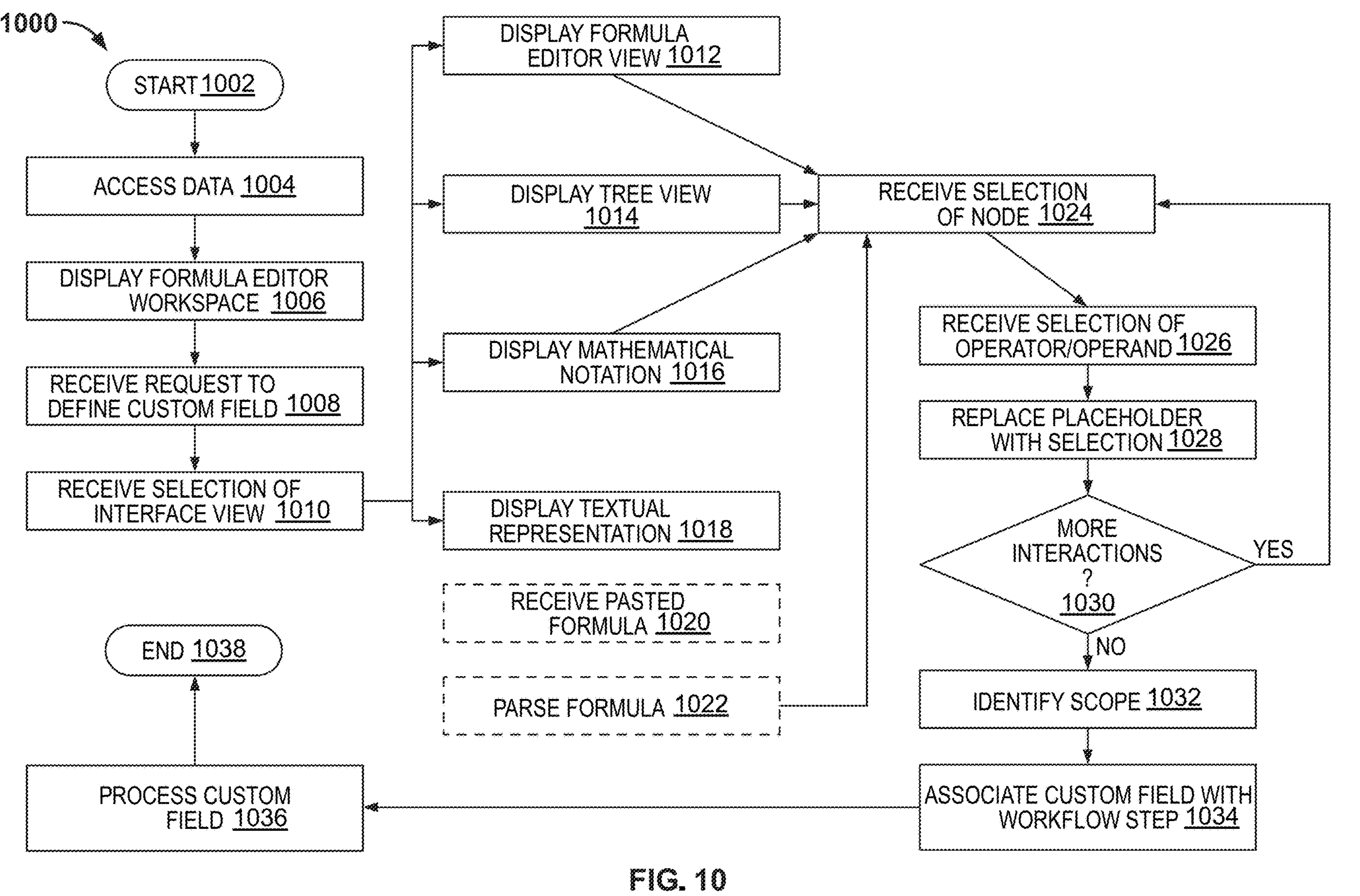
FIG. 10 illustrates exemplary custom field formula logic in accordance with one embodiment.

FIG. 10 is a flowchart depicting exemplary custom field formula logic 1000 for performing a computer-implemented method according to an exemplary embodiment. The logic may be embodied as instructions stored on a computer-readable medium configured to be executed by a processor. The logic may be implemented by a suitable computing system configured to perform the actions described below.

Processing begins at block 1002; for example, processing may begin when a user runs a software application that includes functionality for defining custom field formulas.

In block 1004, the system may access data. The data may be analytical chemistry data generated by one or more laboratory analytical instruments in an analytical chemistry system. The data may be organized into one or more fields.

In block 1006, the system may display formula editor workspace, such as the interface shown in FIG. 4. The formula editor workspace may provide one or more options for creating or editing custom fields for the data accessed at block 1004. The options displayed in the formula editor workspace may depend on the fields in the data and/or the operators and functions supported by the analytical chemistry system.

In block 1008, the system may receive request to define custom field. For example, the system may detect a request from a user to create a new custom field, or to load an existing custom field for viewing and/or editing.

In block 1010, the system may receive a selection of an interface view to be used to view and/or edit the custom field formula.

If the selection is for a formula editor view, then in block 1012 the system may display a formula editor view similar to the one depicted in FIG. 4 (the system may optionally default to this view if no selection is made). If the selection is for a tree view, then at block 1014 the system may represent the custom field formula as a tree, in a tree view similar to the one depicted in FIG. 3. If the selection is for a mathematical, then at block 1016 the system may display a mathematical notation view similar to the one depicted in FIG. 8A and FIG. 8B.

If the selection in block 1010 is a selection of a textual representation view, then in block 1018, the system may display a textual representation of the custom field formula similar to the one depicted in FIG. 7A and FIG. 7B. The textual representation may be displayed in a text box; optionally, in block 1020 the system may receive a pasted formula in the text box and may parse the pasted formula in block 1022, as described above in connection with FIG. 7A and FIG. 7B.

In block 1024, the system may receive a selection of a node in the currently displayed interface view. The node may be an existing node or an interactive placeholder. As noted above, there are different types of interactions that may be performed when a node is selected. For example,

- When an empty node is selected, an operator, a field, or a constant can be added/inserted to the empty node (e.g., using the wizard of FIG. 6). A formula from another custom field can also be inserted into the empty node.
- When the body of a non-empty node is selected, it can be replaced by another (compatible) operator, a field, or a constant. A formula from another custom field can also be inserted into the node. The non-empty node can also be deleted or cleared.
- When the start of a non-empty node is selected, an operator can be inserted to the left of the node, and the original node then becomes the right operand of the newly inserted operator.
- When the end of a non-empty node is selected, and operator can be inserted to the right of the node, and the original node then becomes the left operand of the newly inserted operator.

For the sake of brevity, the remainder of the flowchart assumes that the selected node is an empty interactive placeholder (e.g., the first scenario above). One of ordinary skill in the art will understand that the depicted custom field formula logic 1000 can be readily modified to account for the other scenarios described above.

In block 1026, the system may receive a selection of an operator or operand that should replace the interactive placeholder (block 1028). For instance, the system may display a list of available operators, and a user may select one of the operators in the list to have the selected operator replace the placeholder in the custom field. When an operator is selected, new interactive placeholders representing operands of the operator may be generated and displayed in the selected view. In another example, the system may display a list of available fields or other operands, and a user may select one one of the fields/operands in the list to replace the interactive placeholder.

In decision block 1030, the system determines whether there are more interactions left to process. For instance, if the user selects another node (or the same node as previously edited), then processing may revert to block 1024 and the system may edit the newly selected node. If the user selects another interface view, then processing may revert to block 1010 and the system may display the custom field being edited in the new view.

Before or after the interactions are complete, in block 1032 the system may identify a scope for the custom field formula. For example, the user may specify the scope in a settings interface (see, e.g., FIG. 4 and FIG. 5).

Once editing of the custom field is complete, in block 1034 the system may associate the custom field with a particular workflow stage of an analytical chemistry system. The custom field may have been created in an interface specifically associated with a particular stage of the workflow, which might make certain fields available to the custom field (see, e.g., FIG. 4). In some embodiments, associating the custom field with a workflow stage may involve, in block 1036, processing the custom field with a stage processor.

To process custom fields, the stage processor may perform the following actions

Collect all custom field calculations at a processing stage.

Some custom fields depend on other custom and non-custom fields. The calculations for the fields should thus be ordered by their dependencies.

Parse constants in each formula as scalars.

Loop the injections or components of the experiment according to the "scope" of each calculation to retrieve the fields used in the calculation as vector, and fill the all the nodes that use the same field.

Calculate a result for each node from the bottom up.

Fill any error or warning codes for the custom field.

Processing may then proceed to done block 1038 and terminate.

Although FIG. 10 depicts particular actions performed in a specific order, embodiments are not limited to the configuration shown in FIG. 10. It is contemplated that more, fewer, or different logical blocks may be implemented. Similarly, it is contemplated that the actions may be performed in a different order than the one shown in FIG. 10.

FIG. 11 illustrates one example of a system architecture and data processing device that may be used to implement one or more illustrative aspects described herein in a standalone and/or networked environment. Various network nodes, such as the data server 1110, web server 1106, computer 1104, and laptop 1102 may be interconnected via a wide area network 1108 (WAN), such as the Internet. Other networks may also or alternatively be used, including private intranets, corporate networks, LANs, metropolitan area networks (MANs) wireless networks, personal networks (PANs), and the like. Network 1108 is for illustration purposes and may be replaced with fewer or additional computer networks. A local area network (LAN) may have one or more of any known LAN topology and may use one or more of a variety of different protocols, such as ethernet. Devices data server 1110, web server 1106, computer 1104, laptop 1102 and other devices (not shown) may be connected to one or more of the networks via twisted pair wires, coaxial cable, fiber optics, radio waves or other communication media.

Computer software, hardware, and networks may be utilized in a variety of different system environments, including standalone, networked, remote-access (aka, remote desktop), virtualized, and/or cloud-based environments, among others.

The term "network" as used herein and depicted in the drawings refers not only to systems in which remote storage devices are coupled together via one or more communication paths, but also to stand-alone devices that may be coupled, from time to time, to such systems that have storage capability. Consequently, the term "network" includes not only a "physical network" but also a "content network," which is comprised of the data—attributable to a single entity—which resides across all physical networks.

The components may include data server 1110, web server 1106, and client computer 1104, laptop 1102. Data server 1110 provides overall access, control and administration of databases and control software for performing one or more illustrative aspects described herein. Data server 1110 may be connected to web server 1106 through which users interact with and obtain data as requested. Alternatively, data server 1110 may act as a web server itself and be directly connected to the internet. Data server 1110 may be connected to web server 1106 through the network 1108 (e.g., the internet), via direct or indirect connection, or via some other network. Users may interact with the data server 1110 using remote computer 1104, laptop 1102, e.g., using a web browser to connect to the data server 1110 via one or more externally exposed web sites hosted by web server 1106. Client computer 1104, laptop 1102 may be used in concert with data server 1110 to access data stored therein, or may be used for other purposes. For example, from client computer 1104, a user may access web server 1106 using an internet browser, as is known in the art, or by executing a software application that communicates with web server 1106 and/or data server 1110 over a computer network (such as the internet).

Servers and applications may be combined on the same physical machines, and retain separate virtual or logical addresses, or may reside on separate physical machines. FIG. 11 illustrates just one example of a network architecture that may be used, and those of skill in the art will appreciate that the specific network architecture and data processing devices used may vary, and are secondary to the functionality that they provide, as further described herein. For example, services provided by web server 1106 and data server 1110 may be combined on a single server.

Each component data server 1110, web server 1106, computer 1104, laptop 1102 may be any type of known computer, server, or data processing device. Data server 1110, e.g., may include a processor 1112 controlling overall operation of the data server 1110. Data server 1110 may further include RAM 1116, ROM 1118, network interface 1114, input/output interfaces 1120 (e.g., keyboard, mouse, display, printer, etc.), and memory 1122. Input/output interfaces 1120 may include a variety of interface units and drives for reading, writing, displaying, and/or printing data or files. Memory 1122 may further store operating system software 1124 for controlling overall operation of the data server 1110, control logic 1126 for instructing data server 1110 to perform aspects described herein, and other application software 1128 providing secondary, support, and/or other functionality which may or may not be used in conjunction with aspects described herein. The control logic may also be referred to herein as the data server software control logic 1126. Functionality of the data server software may refer to operations or decisions made automatically based on rules coded into the control logic, made manually by a user providing input into the system, and/or a combination of automatic processing based on user input (e.g., queries, data updates, etc.).

Memory 1122 may also store data used in performance of one or more aspects described herein, including a first database 1132 and a second database 1130. In some embodiments, the first database may include the second database (e.g., as a separate table, report, etc.). That is, the information can be stored in a single database, or separated into different logical, virtual, or physical databases, depending on system design. Web server 1106, computer 1104, laptop 1102 may have similar or different architecture as described with respect to data server 1110. Those of skill in the art will appreciate that the functionality of data server 1110 (or web server 1106, computer 1104, laptop 1102) as described herein may be spread across multiple data processing devices, for example, to distribute processing load across multiple computers, to segregate transactions based on geographic location, user access level, quality of service (QoS), etc.

One or more aspects may be embodied in computer-usable or readable data and/or computer-executable instructions, such as in one or more program modules, executed by one or more computers or other devices as described herein. Generally, program modules include routines, programs, objects, components, data structures, etc. that perform particular tasks or implement particular abstract data types when executed by a processor in a computer or other device. The modules may be written in a source code programming language that is subsequently compiled for execution, or may be written in a scripting language such as (but not limited to) HTML or XML. The computer executable instructions may be stored on a computer readable medium such as a nonvolatile storage device. Any suitable computer readable storage media may be utilized, including hard disks, CD-ROMs, optical storage devices, magnetic storage devices, and/or any combination thereof. In addition, various transmission (non-storage) media representing data or events as described herein may be transferred between a source and a destination in the form of electromagnetic waves traveling through signal-conducting media such as metal wires, optical fibers, and/or wireless transmission media (e.g., air and/or space). Various aspects described herein may be embodied as a method, a data processing system, or a computer program product. Therefore, various functionalities may be embodied in whole or in part in software, firmware and/or hardware or hardware equivalents such as integrated circuits, field programmable gate arrays (FPGA), and the like. Particular data structures may be used to more effectively implement one or more aspects described herein, and such data structures are contemplated within the scope of computer executable instructions and computer-usable data described herein.

The components and features of the devices described above may be implemented using any combination of discrete circuitry, application specific integrated circuits (ASICs), logic gates and/or single chip architectures. Further, the features of the devices may be implemented using microcontrollers, programmable logic arrays and/or microprocessors or any combination of the foregoing where suitably appropriate. It is noted that hardware, firmware and/or software elements may be collectively or individually referred to herein as "logic" or "circuit."

It will be appreciated that the exemplary devices shown in the block diagrams described above may represent one functionally descriptive example of many potential implementations. Accordingly, division, omission or inclusion of block functions depicted in the accompanying figures does not infer that the hardware components, circuits, software and/or elements for implementing these functions would be necessarily be divided, omitted, or included in embodiments.

At least one computer-readable storage medium may include instructions that, when executed, cause a system to perform any of the computer-implemented methods described herein.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

What is claimed is:

1. A computer-implemented method comprising:

accessing data from a laboratory analytical instrument associated with an analytical method encoded in a workflow, the data organized into one or more fields;

receiving a request to define a custom field for use in a stage of the workflow, the custom field representing a field that is not directly or explicitly measured by the laboratory analytical instrument, but derived at least partially from a measured field through a custom field calculation;

displaying, in an interface, a graphical formula editor workspace that comprises a graphical fields list of the one or more fields of the data, a graphical operators list of available operators, and a formula editor displaying a formula comprising an interactive placeholder that represents an empty graphical node into which one of the available operators or one of the available operands can be placed;

performing at least one of:

receiving a selection of one of the available operators from the graphical operators list and incorporating the selected operator into the custom field in place of the empty graphical node of the interactive placeholder, or receiving a selection of one of the one or more fields from the graphical fields list and incorporating the selected field into the custom field in place of the empty graphical node of the interactive placeholder;

converting the custom field built in the graphical formula editor into a tree structure;

validating the tree structure of the custom field;

displaying the custom field in a read-only text format; and associating the custom field with the stage of the workflow, the associating making the custom field accessible to the workflow.

2. The computer-implemented method of claim 1, further comprising computing a value for the custom field during the stage of the workflow.

3. The computer-implemented method of claim 1, wherein the analytical method performs measurements on one or more injections into the laboratory analytical instrument, each injection including one or more components, and further comprising receiving a scope for the custom field, the scope specifying that the custom field calculation should be applied:

to all components in each injection, to each component across all the injections, to all components across all the injections, or to peaks in the data.

4. The computer-implemented method of claim 1, further comprising:

receiving a selection of a tree view interface element; and displaying the custom field as a tree including a set of nodes representing operators and a set of leaf nodes representing operands.

5. The computer-implemented method of claim 1, further comprising:

receiving a selection of a formula renderer interface element; and displaying the custom field in a formula renderer view in a mathematical notation.

6. The computer-implemented method of claim 1, further comprising displaying a textual representation of the custom field in a text box in the interface, wherein the text box is configured to receive a pasted formula from a clipboard but is configured not to allow the formula to be edited within the text box.

7. The computer-implemented method of claim 6, further comprising displaying a cursor at a location in the text box corresponding to a current editing action for the custom field.

8. A non-transitory computer-readable storage medium, the computer-readable storage medium including instructions that when executed by a computer, cause the computer to:

access data from a laboratory analytical instrument associated with an analytical method encoded in a workflow, the data organized into one or more fields;

receive a request to define a custom field for use in a stage of the workflow, the custom field representing a field that is not directly or explicitly measured by the laboratory analytical instrument, but derived at least partially from a measured field through a custom field calculation;

display, in an interface, a graphical formula editor workspace that comprises a graphical fields list of the one or more fields of the data, a graphical operators list of available operators, and a formula editor displaying a formula comprising an interactive placeholder that represents an empty graphical node into which one of the available operators or one of the available operands can be placed;

perform at least one of:

receiving a selection of one of the available operators from the graphical operators list and incorporating the selected operator into the custom field in place of the empty graphical node of the interactive placeholder, or receiving a selection of one of the one or more fields from the graphical fields list and incorporating the selected field into the custom field in place of the empty graphical node of the interactive placeholder;

convert the custom field built in the graphical formula editor into a tree structure;

validate the tree structure of the custom field;

display the custom field in a read-only text format; and associate the custom field with the stage of the workflow, the associating making the custom field accessible to the workflow.

9. The computer-readable storage medium of claim 8, wherein the instructions further configure the computer to compute a value for the custom field during the stage of the workflow.

10. The computer-readable storage medium of claim 8, wherein the analytical method performs measurements on one or more injections into the laboratory analytical instrument, each injection include one or more components, and wherein the instructions further configure the computer to receiving a scope for the custom field, the scope specifying that the custom field calculation should be applied:

to all components in each injection, to each component across all the injections, to all components across all the injections, or to peaks in the data.

11. The computer-readable storage medium of claim 8, wherein the instructions further configure the computer to:

receive a selection of a tree view interface element; and display the custom field as a tree including a set of nodes representing operators and a set of leaf nodes representing operands.

12. The computer-readable storage medium of claim 8, wherein the instructions further configure the computer to:

receive a selection of a formula renderer interface element; and display the custom field in a formula renderer view in a mathematical notation.

13. The computer-readable storage medium of claim 8, wherein the instructions further configure the computer to display a textual representation of the custom field in a text box in the interface, wherein the text box is configured to receive a pasted formula from a clipboard but is configured not to allow the formula to be edited within the text box.

14. The computer-readable storage medium of claim 13, wherein the instructions further configure the computer to display a cursor at a location in the text box corresponding to a current editing action for the custom field.

15. A computing apparatus comprising:

a processor; and a memory storing instructions that, when executed by the processor, configure the apparatus to:

access data from a laboratory analytical instrument associated with an analytical method encoded in a workflow, the data organized into one or more fields;

receive a request to define a custom field for use in a stage of the workflow, the custom field representing a field that is not directly or explicitly measured by the laboratory analytical instrument, but derived at least partially from a measured field through a custom field calculation;

display, in an interface, a graphical formula editor workspace that comprises a graphical fields list of the one or more fields of the data, a graphical operators list of available operators, and a formula editor displaying a formula comprising an interactive placeholder that represents an empty graphical node into which one of the available operators or one of the available operands can be placed;

perform at least one of:

receiving a selection of one of the available operators from the graphical operators list and incorporating the selected operator into the custom field in place of the empty graphical node of the interactive placeholder, or receiving a selection of one of the one or more fields from the graphical fields list and incorporating the selected field into the custom field in place of the empty graphical node of the interactive placeholder;

convert the custom field built in the graphical formula editor into a tree structure;

validate the tree structure of the custom field;

display the custom field in a read-only text format; and associate the custom field with the stage of the workflow, the associating making the custom field accessible to the workflow.

16. The computing apparatus of claim 15, wherein the instructions further configure the apparatus to compute a value for the custom field during the stage of the workflow.

17. The computing apparatus of claim 15, wherein the analytical method performs measurements on one or more injections into the laboratory analytical instrument, each injection include one or more components, and wherein the instructions further configure the apparatus to receiving a scope for the custom field, the scope specifying that the custom field calculation should be applied:

to all components in each injection, to each component across all the injections, to all components across all the injections, or to peaks in the data.

18. The computing apparatus of claim 15, wherein the instructions further configure the apparatus to:

receive a selection of a tree view interface element; and display the custom field as a tree including a set of nodes representing operators and a set of leaf nodes representing operands.

19. The computing apparatus of claim 15, wherein the instructions further configure the apparatus to:

receive a selection of a formula renderer interface element; and display the custom field in a formula renderer view in a mathematical notation.

20. The computing apparatus of claim 15, wherein the instructions further configure the apparatus to display a textual representation of the custom field in a text box in the interface, wherein the text box is configured to receive a pasted formula from a clipboard but is configured not to allow the formula to be edited within the text box.

* * * * *